United States Patent [19]

Gartz

[11] Patent Number: 5,084,020

[45] Date of Patent: Jan. 28, 1992

[54] CANNULA DEVICE WITH MEANS TO PROVIDE SAFE STORAGE AFTER USE

[75] Inventor: Kaj Gartz, Orange, Conn.

[73] Assignee: Owen J. Meegan, Salem, Mass. ; a part interest

[21] Appl. No.: 621,287

[22] Filed: Nov. 30, 1990

[51] Int. Cl.⁵ .............................................. A61M 5/00
[52] U.S. Cl. ..................... 604/110; 604/192; 604/240
[58] Field of Search ............... 604/110, 162, 167, 192, 604/198, 263, 240, 243, 195; 239/195, 198; 43/20

[56] References Cited

U.S. PATENT DOCUMENTS

| | | | |
|---|---|---|---|
| 3,419,992 | 1/1969 | Strahm | 43/20 |
| 3,472,456 | 10/1969 | Strong | 239/198 |
| 3,747,812 | 7/1973 | Karman . | |
| 3,893,608 | 7/1975 | Koenig . | |
| 4,266,544 | 5/1981 | Wardlaw . | |
| 4,273,123 | 6/1981 | Lemelson . | |
| 4,428,139 | 1/1984 | Henze et al. | 43/20 |
| 4,582,257 | 4/1986 | Siegler | 239/198 |
| 4,634,428 | 1/1987 | Cuu . | |
| 4,804,370 | 2/1989 | Haber et al. | 604/110 |
| 4,978,340 | 12/1990 | Terrill et al. | 604/110 |

FOREIGN PATENT DOCUMENTS

| | | | |
|---|---|---|---|
| 2634651 | 2/1990 | France | 604/192 |
| 8911304 | 11/1989 | World Int. Prop. O. . | |

Primary Examiner—C. Fred Rosenbaum
Assistant Examiner—Sharon Finkel
Attorney, Agent, or Firm—Owen J. Meegan

[57] ABSTRACT

A disposable device for the use, destruction and storage of a cannula useful for placement in blood vessels. The device includes a housing for the cannula with apertures through which the cannula extends and is slidably disposed. The cannula is fixedly disposed through a reel that is fitted in a cavity in the housing. The reel has an axis of rotation at right angles to the cannula and turning the reel wraps the cannula around the reel to deform, destroy and store it. The points of the cannula will be withdrawn into the housing through the apertures. When the points are fully withdrawn they will snap against the inside of the housing to provide sensory indications that the device can be handled safely.

25 Claims, 2 Drawing Sheets

CANNULA DEVICE WITH MEANS TO PROVIDE SAFE STORAGE AFTER USE

BACKGROUND OF THE INVENTION

The present invention relates to a device for the safe destruction and storage of used cannulas and especially for devices that are adapted to be used with double ended cannulas which are made for sampling blood and injecting therapeutic medications and adapted to be used only once.

Cannulas and equipment used for sampling blood and injecting therapeutic fluids frequently are disposable and designed to be discarded after a single use. Once a cannula has been used to draw blood or inject a medication, it is contaminated. The sharp point on a contaminated needle can injure people and cause the spread of disease among those that handle it. Infectious diseases such as HIV or hepatitis viruses have been transmitted to people who handle contaminated needles and accidentally stick themselves with them. Small residues of blood and viruses on the cannula from an infected patient can result in transmission of a disease that the patient has contracted to a staff member.

In the past, relatively complex arrangements have been devised to prevent the accidental infections from contaminated needles. I have found that covering of sharp points and destruction of the cannula to prevent reuse is highly desirable because hypodermic needles are frequently reused by drug abusers and accidental contact or intentional use must be eliminated.

Exemplary of devices which have attempted to solve these problems is the application of Ameur: Int. Pub. No. WO89/11304; PTC/SE89/00290. The application discloses a pair of protective sleeves that are displaceable in a longitudinal direction over a holder that is provided for a double pointed cannula. The sleeves serve as adapters that provide a bayonet socket which is fitted into another bayonet socket. The arrangement is used with a sample holder which has steps formed in an end to receive a peg that holds the arrangement together during use. As viewed, the sleeves of the cannula can easily move and expose the needle after use when it is contaminated. Moreover, the arrangement requires the provision for a specially designed sample holding device to accommodate the sleeves and even with this fairly complex combination, the needle is not destroyed after use.

In the Wardlaw U.S. Pat. No. 4,366,544, patentee describes a hypodermic syringe which has provision for preventing more than one use and rendering the needle inoperative. According to the Wardlaw patent, a mechanism is mounted on the syringe which, after administering the injection, is manipulated to bend the needle of the syringe at a right angle and concurrently retract it from its normally projecting position to a second position in which it is housed in a cavity. The retraction is accomplished by twisting a cap around a post so that the needle is permanently deformed and wrapped around the post. While protection of the needle point and destruction of the needle is provided with the mechanism, significant torque is required to twist the cap to urge the needle around the post to destroy and house it. The amount of torque necessary to accomplish the wrapping and housing can exceed the strength of the various plastic parts.

Capping arrangements such as shown in Lemelson U.S. Pat. No. 4,273,123; Karmen et al U.S. Pat. No. 3,747,812; and Cuu U.S. Pat. No. 4,634,428, all involve an ancillary cap over the cannula to bend or distort the metal. Similarly, the Koening U.S. Pat. No. 3,893,608, discloses a syringe that is fitted onto a cover to distort it through the placement of a post surrounding by an annular ring.

SUMMARY OF THE INVENTION

According to the present invention, I have found that the disposition of a cannula in a hollow housing and through a reel fitted in the housing can enable the user to simultaneously destroy the cannula, store it and prevent accidental contact with the sharp points of the needle. The device is preferably formed of molded styrene, polycarbonates, polyamides or polyethylene and can be attached to a conventional sample holder in conventional ways, generally by threading it on. After use, the reel can be turned to wrap the cannula around it and the exposed end(s) of the cannula is wrapped about the reel. In the preferred embodiment (with a double ended needle) when the reel is turned, the cannula is drawn into the hollow housing and one portion is wrapped around the reel in a clockwise direction and the other is wrapped in a counterclockwise direction. The wrapping causes the sharp points of the cannula to be drawn into the cavity of the housing. When completely drawn into the housing, I have further found that a positive indication of complete covering of the sharp points is provided by the feel and sound of them snapping against the inside of the housing which indicates that the device is safe to be disposed of without injury.

DESCRIPTION OF THE PREFERRED EMBODIMENTS

Figure 1:
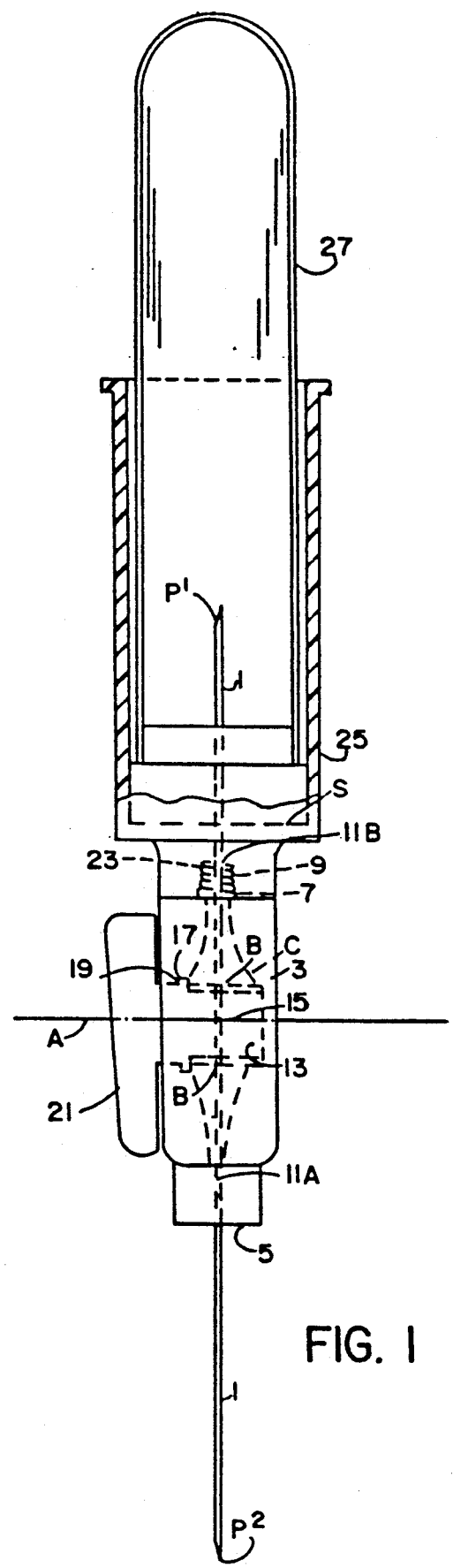
FIG. 1 is a side elevational view partially in cross-section of an embodiment of the disposable device for the use, destruction and storage of a cannula.

Referring now to FIG. 1, a cannula 1 having sharp end points, herein called dispensing point $P^1$ and receiving point $P^2$ is shown fitted in a housing 3. The housing 3 has a first end 5 and a second end 7. The second end 7 terminates in a threaded nipple 9. One end of the cannula 1 is slidably disposed in an aperture 11A that is formed in the first end 5 and the other end of the cannula 1 slidably disposed in another aperture 11B that is formed in the second end 7.

The cannula 1 is fixedly disposed in a throughhole 15 that is formed in reel 13. Reel 13 is rotatably disposed in the housing 3 and rotates about an axis A. The axis of rotation of the reel 13 is preferably at right angles to the cannula 1 so that when the reel 13 is turned on its axis, the cannula 1 bends at point B and then wraps around reel 13. Since cannula 1 is slidably disposed within the apertures 11A and 11B, the points P¹ and P² can be retracted into housing 3.

Preferably, a flange 17 is disposed on the side of the reel 13 and fits into a recess 19 to insure easy rotation and to prevent the reel 13 from falling out of the housing. A handle 21 is attached to reel 13 to enable the user to turn it. In the embodiment shown, the threaded nipple 9 is screwed into an internally threaded end 23 of a conventional holder 25. A conventional vacuum tube 27 is shown with a stopper S fitted into its open end. In use, the receiving point P² is inserted into a patient's blood vessel. Dispensing point P¹ of cannula 1 is forced through stopper S and blood will pass through the receiving point P² into the cannula 1 to emerge from the dispensing point P¹ and into the vacuum tube 27. A multiplicity of different vacuum tubes 27 are frequently used in medical facilities and they are serially disposed on cannula 1 to take samples for different tests. After the required number of samples have been taken, the last vacuum tube is removed from the holder 25 and the cannula 1 is withdrawn from the patient. The handle 21 is then turned on axis A to cause the cannula 1 to wrap around the reel 13 and withdraw through apertures 11A and 11B, as will be described hereinafter.

Figure 2:
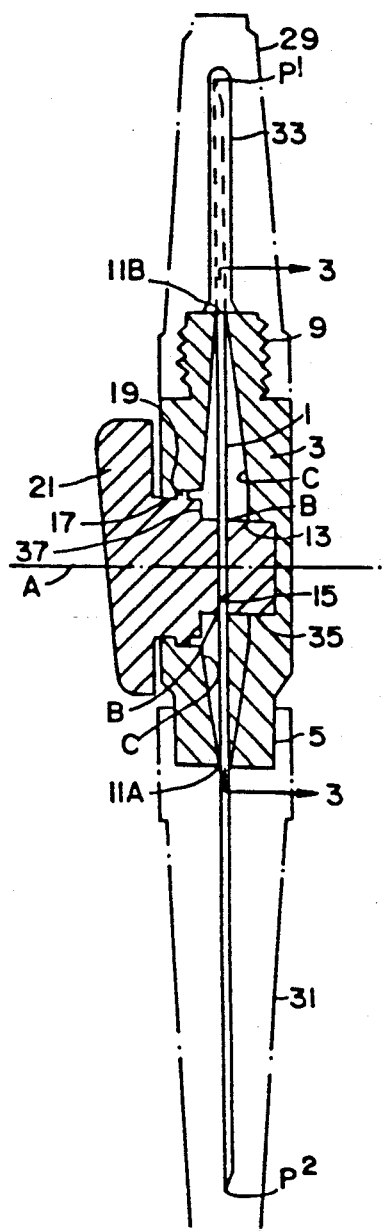
FIG. 2 is a cross-sectional view of the device shown in FIG. 1.

Referring now to FIG. 2, the device of the present invention is shown in cross-section. The device includes the housing 3 in which is disposed the cannula 1. A cavity C is formed within the housing 3 to provide room for the wrapped cannula 1. As shown, a cover 29 fits over the dispensing point P¹ and another cover 31 fits over the receiving point P². Cover 31 is slidably disposed over first end 5 and cover 29 is threaded onto nipple 9. As is well known, usually a rubber shield 33 is fitted over dispensing point P¹. When a vacuum tube is forced over dispensing point P¹ the rubber shield 33 is urged back and slides along cannula 1 ahead of the stopper to prevent blood from leaking from the end of the dispensing point P¹ as vacuum tubes are being changed to secure samples. When one vacuum tube is removed and before another is put on, the shield 33 will slide back into its original position to cover point P¹ and then will slide back ahead of the next stopper that is to be filled.

As mentioned previously, the reel 13 is rotatably disposed within the housing 3. One side of the reel 13 is disposed within the fitting 35 that is formed inside of the housing 3 and the other side has flange 17 that is disposed within recess 19. A shoulder 37 is formed on the side of reel 13 to receive the cannula 1 as it is being destroyed by twisting handle 21 after use. The cannula 1 is fixedly disposed in the throughhole 15 so that when the point P² is being inserted into the patient being tested, it will not slide upwardly. Also, the fixed disposition of cannula 1 in throughhole 15 prevents the point P¹ from moving as a vacuum tube is forced onto it. Such fixed disposition can be easily accomplished by using well known adhesives that bind metal to plastic.

Figure 3:
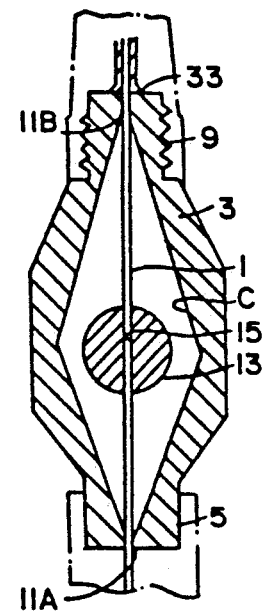
FIG. 3 is cross-sectional view taken along the lines 3—3 of FIG. 2.

As shown in FIG. 3, the cannula 1 is disposed in the throughhole 15 that preferably passes through the diameter of the reel 13. As set out previously, cannula 1 is preferably disposed at right angles to the axis of rotation A of reel 13. Cavity C is large enough to receive all of the destroyed cannula 1. Cavity C preferably is shaped so that there is a greater amount of freeboard space on the longitudinal axis than on the lateral axis.

Figure 4:
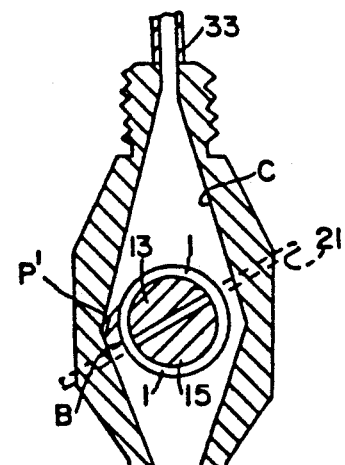
FIG. 4 is the same cross-sectional view taken as FIG. 3, except that in FIG. 4, the cannula is shown destroyed and disposed within the device.

As shown in FIG. 4, the internal shape of cavity C causes the point P¹ (and P², not shown) to engage and then disengage the sides so that when the handle 21 is turned to wrap cannula 1 around reel 13 and the point P¹ (and P²) is fully retracted, it snaps against the inside to produce sensory indications of full withdrawal. The used, destroyed cannula 1 is thus wrapped and safely stored on reel 13. In the illustration a clockwise rotation of the handle 21 is shown but counterclockwise rotation is equally effective. When fully retracted into the housing 3 the device can be readily handled without fear of having points accidently stick the person who is working with it. If desired, the cover 29 over point P¹ and the cover 31 over point P² can be redisposed on the device but such redisposition is not necessary.

Figure 5:
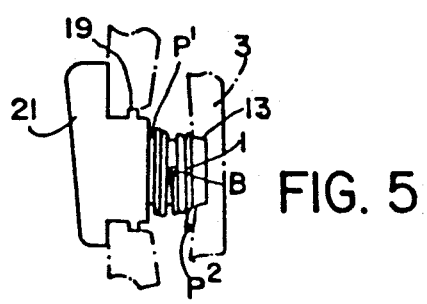
FIG. 5 is a side view of the reel and handle shown in FIG. 4 with the destroyed cannula wound upon the reel.

As shown in FIG. 5, the cannula 1 is wrapped around reel 13. Cannula 1 emerges from throughhole 15 and wraps initially at bend B. In the embodiment shown, the portion of the cannula to the right of throughhole 15 is wrapped in one direction and the portion to the left of throughhole 15 is wrapped in the opposite direction. While a neat winding of the cannula 1 is shown around reel 13, such disposition of the cannula 1 is not necessary and it may not even occur. The number of turns necessary to fully retract points P¹ and P² into the housing is a function of the length of the cannula 1 and the diameter of the reel 13 and may be varied as desired.

It is apparent that modifications and changes can be made within the spirit and scope of the present invention but is my intention, however, only to be limited by the scope of the appended claims.

As my invention, I claim:

1. A disposable device for the use, destruction and storage of a cannula, said device comprising:
   a cannula having at least one point;
   a hollow housing for said cannula, said housing having interior walls and at least one aperture at an end thereof, said cannula being slidably disposed in said aperture and extending therefrom; and
   storage means having an axis of rotation for deforming and storing the deformed cannula, said storage means being disposed within said housing, said storage means further fixedly disposing said cannula relative said axis and rotatably receivable of said cannula whereby rotation of said storage means about said axis causes retraction of said point into said housing and wrapping of said cannula around said storage means;
   means to enable said storage means to be rotated.

2. The device according to claim 1 wherein the axis of rotation of said storage means is at right angles to said cannula.

3. The device according to claim 1 further including fastener means disposed at an end of said housing whereby to enable said device to be attached to a holder.

4. The device according to claim 1 wherein said aperture is disposed relative to said housing so that when said point is fully retracted housing through said aperture, the point snaps against said interior walls to provide sensory indications that it is fully withdrawn.

5. A disposable device for the use, destruction and storage of a cannula, said device comprising:
   a cannula having two opposite ends with a point at each end;
   a housing for said cannula, said housing having apertures at opposite ends thereof, said cannula extending from and slidably disposed within each of the apertures;
   storage means disposed inside said housing to fixedly receive said cannula, said storage means having an axis of rotation, the rotation of said storage means causing retraction of the points of said cannula through the apertures and into said housing; and means to enable said storage means to be rotated.

6. The device according to claim 5 wherein the axis of rotation of said storage means is at right angles to said cannula.

7. The device according to claim 5 wherein said housing is hollow with interior walls and wherein said aperture is disposed relative to said interior walls whereby when said points are fully retracted into said hollow housing, the points snap against said interior walls to provide sensory indications that they are fully retracted.

8. The device according to claim 5 wherein a throughhole is disposed within said storage means whereby to hold said cannula.

9. The device according to claim 8 wherein said cannula is fixedly disposed in said throughhole.

10. The device according to claim 5 further including fastener means disposed at one of said ends of said housing whereby to enable said device to be attached to a holder.

11. The device according to claim 5 further including a flange fixedly disposed on a side of said storage means and a recess disposed in said housing, said recess being adapted to receive said flange whereby to enable said storage means to be rotated about its axis.

12. The device according to claim 5 wherein the circumference of said storage means is sufficient to hold the cannula wrapped around it when said points are fully retracted into said housing.

13. A disposable device for the use, destruction and storage of a cannula, said device comprising:
 a cannula having two points;
 a housing for said cannula, said housing having an aperture at opposite ends thereof, said cannula extending from said apertures;
 reel means centrally disposed within said housing and a throughhole disposed in said reel means and passing therethrough, said cannula being fixedly disposed in said throughhole and passing through said reel means; and
 means to rotate said reel means, said rotation means being disposed externally of said housing whereby rotation of said reel means causes said cannula to wrap itself around said reel and retract through said apertures into said housing.

14. The device according to claim 13 wherein the axis of said reel means is disposed at right angles to said cannula.

15. The device according to claim 13 further including fastener means disposed at one of said ends whereby to enable said device to be attached to a holder.

16. The device according to claim 13 further including a flange fixedly disposed on a side of said reel means and a recess disposed in said housing, said flange being rotatably disposed in said recess whereby to enable said reel means to be rotated about its axis.

17. The device according to claim 13 wherein said housing is hollow with interior walls and wherein said aperture is disposed relative to said walls, whereby when said points are fully retracted into said hollow housing, the points snap against said interior walls to provide sensory indications that they are fully retracted.

18. A device to obtain samples of blood or injecting therapeutic medications, said device having a cannula with at least one point characterized in that a portion of the cannula is disposed within a housing having a reel rotatably fitted therein and the cannula is fixedly disposed in the reel and means to wrap the cannula around said reel to destroy and store it.

19. The device according to claim 18 wherein said housing is hollow with interior walls and an aperture, said aperture being disposed relative to said interior walls, whereby when said point is fully retracted into said hollow housing, the point snaps against said interior walls of said housing to provide sensory indications that it is fully retracted.

20. A device for the destruction and safe storage of a cannula after use, said device comprising a reel rotatably disposed in a housing, said cannula being held by said reel; means to retract, destroy and store said cannula, whereby when said reel is rotated, the cannula will be retracted into said housing and wound upon said reel to destroy and store it.

21. The device according to claim 20 wherein said housing is hollow having interior walls, whereby when said cannula is fully retracted into said hollow housing, it snaps against said interior walls to provide sensory indications that it is fully retracted.

22. The device according to claim 20 wherein said housing has a longitudinal axis passing through said aperture and said cannula is retracted into said housing on said longitudinal axis.

23. A device for the destruction and safe storage of a cannula after use, said device comprising;
 a housing having at least one aperture therein, said cannula being partially disposed in said housing and being slidably disposed in said aperture and projecting outwardly therefrom;
 means to retract, destroy and house said cannula, said cannula being held by said means, said means having an axis of rotation and being disposed within said housing for retracting the projecting portion of said cannula through said aperture upon rotation.

24. The device according to claim 23 wherein said housing is hollow with interior walls therein whereby when said cannula is fully retracted through said aperture and into said hollow housing, it engages the interior walls to provide sensory indications that it is fully retracted into said housing.

25. The device according to claim 23 wherein said housing has a longitudinal axis passing through said aperture and said cannula is retracted into said housing on said longitudinal axis.

* * * * *